United States Patent
Lee et al.

(10) Patent No.: US 9,637,717 B2
(45) Date of Patent: May 2, 2017

(54) METHOD AND APPARATUS FOR THE USE OF MICRO-CARRIERS IN A DISPOSABLE BIOREACTOR SYSTEM

(71) Applicant: PBS BIOTECH, Inc., Camarillo, CA (US)

(72) Inventors: Chanyong Brian Lee, Camarillo, CA (US); Yasunori Hashimura, Camarillo, CA (US)

(73) Assignee: PBS Biotech, Inc., Camarillo, CA (US)

( * ) Notice: Subject to any disclaimer, the term of this patent is extended or adjusted under 35 U.S.C. 154(b) by 210 days.

(21) Appl. No.: 14/153,679

(22) Filed: Jan. 13, 2014

(65) Prior Publication Data

US 2014/0196791 A1    Jul. 17, 2014

Related U.S. Application Data

(60) Provisional application No. 61/751,339, filed on Jan. 11, 2013.

(51) Int. Cl.
*C12M 3/00* (2006.01)
*C12M 1/12* (2006.01)
(Continued)

(52) U.S. Cl.
CPC ............ *C12M 25/16* (2013.01); *C12M 27/06* (2013.01); *C12M 29/04* (2013.01); *C12M 41/00* (2013.01); *Y10T 137/0318* (2015.04)

(58) Field of Classification Search
CPC ...... C12M 23/14; C12M 23/58; C12M 25/16; C12M 25/20; C12M 27/02; C12M 33/14; C12N 5/0075
See application file for complete search history.

(56) References Cited

U.S. PATENT DOCUMENTS 5,707,859 A    1/1998  Miller et al.
7,628,528 B2   12/2009 Zeikus
(Continued)

FOREIGN PATENT DOCUMENTS

GB     2163453        2/1986
WO  2008133845 A2   11/2008
WO  2009132192 A2   10/2009

OTHER PUBLICATIONS

European Patent Office, International Search Report and Written Opinion for Application No. PCT/US2014/011313, Mail Date May 2, 2014.

*Primary Examiner* — William H Beisner
(74) *Attorney, Agent, or Firm* — SoCal IP Law Group LLP; Guy L. Camberbatch; Steven C. Sereboff

(57) ABSTRACT

A system and method for compartmentalizing micro-carriers in a bioreactor includes a container configured to store micro-carriers and a vessel configured to contain a fluid so as to prevent the micro-carriers from entering the vessel during sterilization, shipping, storage, or other pre-use handling of the system. One or more addition lines connect the container and the vessel such that the vessel is in fluid communication with the vessel. The one or more addition lines are contactable by at least one blocking element configured to reversibly block fluid flow between the container and the vessel. The container, addition lines, and vessel are configured to allow the micro-carriers to be injected into the vessel at any point during a cell culture run. The vessel may also include a rotatable wheel, a harvest port configured to allow for the removal of the micro-carriers from the vessel, and a media removal port comprising a retention screen for removing spent medium.

26 Claims, 7 Drawing Sheets

(51) Int. Cl.
    *C12M 1/06*     (2006.01)
    *C12M 1/00*     (2006.01)
    *C12M 1/34*     (2006.01)

(56) References Cited

U.S. PATENT DOCUMENTS

| | | |
|---|---|---|
| 7,713,730 B2 | 5/2010 | Zeikus et al. |
| 7,819,576 B2 | 10/2010 | Zeikus |
| 8,281,672 B2 | 10/2012 | Lee et al. |
| 2008/0261299 A1 | 10/2008 | Zeikus et al. |
| 2009/0269849 A1 | 10/2009 | Lee et al. |
| 2011/0003366 A1 | 1/2011 | Zeikus |

METHOD AND APPARATUS FOR THE USE OF MICRO-CARRIERS IN A DISPOSABLE BIOREACTOR SYSTEM

PRIORITY CLAIM

This application claims the benefit under 35 U.S.C. §119(e) of U.S. Provisional Application No. 61/751,339, filed Jan. 11, 2013, the disclosure of which is hereby incorporated by reference in its entirety.

FIELD OF INVENTION

This invention relates to a system and a method for compartmentalizing micro-carriers. Specifically, the invention relates to a bioreactor system that comprises a micro-carrier container for storing micro-carriers that is separate from a bioreactor vessel chamber, wherein the pouch and the vessel are in fluid connection, and a method for providing sterilized micro-carriers to a sterilized vessel chamber.

BACKGROUND

In early-stage research where the total number of cells required from a cell culture run are relatively small, adherent-based cells may be grown on cell culture vessels with flat surfaces such as T-flasks or roller bottles that have been surface-treated with substrates required for cell attachment. However, scaling up to larger volumes in these flat culture vessels quickly becomes impractical from the standpoint of vessel footprint, processing time, and media costs.

Micro-carriers are small (typically 100-200 micron in diameter), surface-treated spheres that serve as scaffolds for anchorage-dependent cells to attach and grow on while being suspended in bioreactor systems. They are ideal for scaling up anchorage-dependent cells, as they greatly increase the surface area for cells to grow on by utilizing the entire volume of the bioreactor instead of just the outer surfaces of the vessels, as in flat culture vessels. Prior to use in a bioreactor, micro-carriers are typically hydrated in phosphate buffered saline solution and then heat-sterilized in bottles in an autoclave prior to transfer into a bioreactor via an aseptic connection.

Single-use bioreactors consist of disposable vessels that have been pre-sterilized by the manufacturer, typically by gamma radiation, to eliminate the cleaning requirements by the end user. Micro-carriers that can withstand gamma radiation at sterilization dosage may be pre-loaded inside the disposable bioreactor vessel assembly by the manufacturer for sterilization by gamma radiation prior to shipping. The end user would then simply add medium aseptically and allow the micro-carriers to hydrate while being mixed prior to inoculation with cells.

SUMMARY OF INVENTION

According to exemplary embodiments, a bioreactor system for compartmentalizing micro-carriers is provided. More specifically, aspects of the invention are embodied in a bioreactor system that comprises a micro-carrier container configured to store micro-carriers, a vessel configured to contain a fluid, and one or more fluid conduit lines connecting the micro-carrier container and the vessel such that the micro-carrier container is in fluid communication with the vessel. The one or more fluid conduit lines may be reversibly blocked to block fluid flow in the one or more lines. The micro-carrier container and the vessel may be configured to allow the micro-carriers to be dropped into the vessel at any point during a cell culture procedure when the one or more fluid conduit lines are unblocked.

According to further aspects of the invention, the micro-carrier container may comprise a pouch connected to the one or more fluid conduit lines.

According to further aspects of the invention, the one or more fluid conduit lines may comprise a main addition line and the micro-carrier container may terminate the main addition line. The system may further comprise a reversible flow blocking element disposed on the main addition line between the micro-carrier container and the vessel and configured to temporarily prevent micro-carriers from passing through the main addition line from the micro-carrier container to the vessel. The micro-carrier container, the vessel, the main addition line, and the blocking element may be further configured such that gravitational force is sufficient to cause micro-carriers to pass from the micro-carrier container to the vessel via the main addition line.

According to further aspects of the invention, the one or more fluid conduit lines may comprise an addition line and the micro-carrier container may be disposed in-line with the addition line. The system may further comprise a first reversible flow blocking element disposed on the addition line prior to the micro-carrier container and configured to control fluid flow into the micro-carrier container, and a second reversible flow blocking element disposed on the addition line between the micro-carrier container and the vessel and configured to control a flow of a fluid mixture comprising micro-carriers from the micro-carrier container to the vessel. The micro-carrier container, the addition line, and the first reversible flow blocking element, may be configured for selective addition of fluid into the micro-carrier container through a portion of the addition line so that micro-carriers contained in the micro-carrier container become dispersed in the fluid. The micro-carrier container, the addition line, the second reversible flow blocking element, and the vessel may also be configured for selective addition of a fluid mixture comprising micro-carriers from the micro-carrier container through a portion of the addition line and into the vessel.

According to further aspects of the invention, the one or more fluid conduit lines may comprise a branched addition line and the micro-carrier container may be disposed in-line with the branched addition line, and a primary addition line connected to the vessel. The system may further comprise a first reversible flow blocking element disposed on the branched addition line prior to the micro-carrier container and configured to control fluid flow into the micro-carrier container, a second reversible flow blocking element disposed on the branched addition line between the micro-carrier container and the vessel and configured to control a flow of a fluid mixture comprising micro-carriers from the micro-carrier container to the vessel, and a third reversible flow blocking element disposed on the primary addition line and configured to control fluid flow through the primary addition line and into the vessel. The branched addition line, the primary addition line, the first reversible flow blocking element, the third reversible flow blocking element, and the vessel may be configured for selective addition of fluid into the vessel through the primary addition line while blocking fluid flow into the micro-carrier container. The branched addition line, the primary addition line, the first reversible flow blocking element, the third reversible flow blocking element, and the micro-carrier container may be configured for selective addition of fluid into the micro-carrier container through a portion of the branched addition line while blocking fluid flow through the primary addition line so that micro-carriers contained in the micro-carrier container become dispersed in the fluid. The branched addition line, the second reversible flow blocking element, the micro-carrier container, and the vessel may be configured for selective addition of a fluid mixture comprising micro-carriers from the micro-carrier container through a portion of the branched addition line and into the vessel.

According to further aspects of the invention, the one or more fluid conduit lines may be reversibly blocked by one or more clamps.

According to further aspects of the invention, the bioreactor system may further comprise micro-carriers disposed within the micro-carrier container.

According to further aspects of the invention, the micro-carrier container, the vessel, the micro-carriers, and the one more fluid conduit lines may be sterilized.

According to exemplary embodiments, the vessel may comprise a curved bottom. The system may further comprise a mixing wheel rotatably disposed within the vessel, at least one sparger port configured to inject gas into the vessel, a harvest port configured to allow for the removal of cultured cell material from the vessel, and a media removal port configured for removing fluid media from the vessel and comprising a retention screen. The retention screen may be configured to retain the micro-carriers in the vessel while fluid media is removed from the vessel via the media removal port.

According to further aspects of the invention, the mixing wheel may be configured to be pneumatically driven and the at least one sparger port may comprise a main sparger port configured to inject gas into the vessel below the mixing wheel to pneumatically drive rotation of the mixing wheel.

According to further aspects of the invention, the retention screen may comprise a plurality of pores formed in a convex manner with respect to a fluid media side of the retention screen and having a perimeter that is raised toward an interior of the vessel.

According to further aspects of the invention, the vessel may be a rigid or semi-rigid tank, or a flexible or partially flexible bag.

According to further aspects of the invention, the one or more fluid conduit lines may comprise at least one aseptic connection device.

According to further aspects of the invention, the micro-carrier container may comprise a segregatable portion of the one or more conduit lines According to exemplary embodiments, a method for compartmentalizing micro-carriers in a bioreactor system is provided. More specifically, aspects of the invention are embodied in a bioreactor system that may comprise a micro-carrier container, a vessel, and one or more fluid conduit lines connecting the micro-carrier container and the vessel such that the micro-carrier container is in fluid communication with the vessel. Aspects of the invention are embodied in a method that may comprise placing the micro-carriers in the micro-carrier container so that the micro-carriers are separated from the vessel, reversibly blocking the fluid communication between the micro-carrier container and the vessel to retain the micro-carriers in the micro-carrier container, and sterilizing the vessel and the micro-carriers stored within the micro-carrier container.

According to further aspects of the invention, the step of sterilizing may comprise exposing the vessel and micro-carriers to sterilizing gamma radiation.

According to further aspects of the invention, the method may further comprise the step of aseptically packaging the sterilized vessel and the micro-carriers prior to adding fluid to the vessel.

According to further aspects of the invention, the method may further comprise the steps of adding a fluid to the vessel, reversing the fluid communication block between the micro-carrier container and the vessel, and moving the micro-carriers from the micro-carrier container into the vessel through the fluid communication between the micro-carrier container and the vessel.

According to further aspects of the invention, the one or more fluid conduit lines may comprise a main addition line connected to the vessel, the micro-carrier container may terminate the main addition line, and the main addition line may be reversibly blocked between the micro-carrier container and the vessel to temporarily prevent micro-carriers from passing through the main addition line from the micro-carrier container to the vessel. The method may further comprise adding a fluid to the vessel, reversing the reversible block in the main addition line between the micro-carrier container, and moving the micro-carriers from the micro-carrier container into the vessel via the main addition line between the micro-carrier container and the vessel.

According to further aspects of the invention, the micro-carriers may be moved from the micro-carrier container to the vessel via gravity.

According to further aspects of the invention, the one or more fluid conduit lines may comprise an addition line, the micro-carrier container may be disposed in-line with the addition line, the addition line may be reversibly blocked prior to the micro-carrier container to control fluid flow into the micro-carrier container, and the addition line between the micro-carrier container and the vessel may be reversibly blocked to control a flow of a fluid mixture comprising micro-carriers from the micro-carrier container to the vessel. The method may further comprise adding fluid to the vessel, reversing the reversible block in the addition line prior to the micro-carrier container, adding fluid to the micro-carrier container via the addition line, while maintaining the reversible block in the addition line between the micro-carrier container and the vessel, reversing the reversible block in the addition line between the micro-carrier container and the vessel, and moving a mixture comprising micro-carriers from the micro-carrier container into the vessel via the addition line between the micro-carrier container and the vessel.

According to further aspects of the invention, the one or more fluid conduit lines may comprise a branched addition line and a primary addition line connected to the vessel, the micro-carrier container may be disposed in-line with the branched addition line, the branched addition line may be reversibly blocked prior to the micro-carrier container to control fluid flow into the micro-carrier container, the branched addition line may be reversibly blocked between the micro-carrier container and the vessel to control a flow of a fluid mixture comprising micro-carriers from the micro-carrier container to the vessel, and the primary addition line may be reversibly blocked to control fluid flow through the primary addition line and into the vessel. The method may further comprise removing the reversible block in the primary addition line, adding fluid to the vessel via the primary addition line, while maintaining the reversible blocks in the branched addition line, removing the reversible block in the branched addition line prior to the micro-carrier container, adding fluid to the micro-carrier container via the branched addition line, while maintaining the reversible block in the branched addition line between the micro-carrier container and the vessel, removing the reversible block in the branched addition line between the micro-carrier container and the vessel, and moving a mixture comprising micro-carriers from the micro-carrier container into the vessel via the branched addition line between the micro-carrier container and the vessel.

According to further aspects of the invention, the vessel may comprise a curved bottom. The bioreactor system may further comprise a mixing wheel rotatably disposed within the vessel, at least one sparger port configured to inject gas into the vessel, a harvest port configured to allow for the removal of cultured cell material from the vessel, and a media removal port configured for removing fluid media from the vessel and comprising a retention screen to retain the micro-carriers in the vessel while removing fluid media via the media removal port. The method may further comprise injecting a gas into the vessel via the at least one sparger port to pneumatically drive the rotatable mixing wheel, thereby creating a tangential flow of fluid between a periphery of the mixing wheel and the curved surface, and removing fluid from the vessel via the media removal port, while the retention screen retains micro-carriers in the vessel.

According to further aspects of the invention, the method may further comprise the step of removing the micro-carriers via the harvest port.

According to further aspects of the invention, the bioreactor system may further comprise one or more additional ports, and the method may further comprise the step of injecting a fluid through the one or more additional ports to create a steady-state equilibrium of fluid volume within the vessel.

According to further aspects of the invention, the fluid added to the micro-carrier container may be a cell culture medium, a nutrient solution, phosphate buffered saline, or water.

Other features and characteristics of the present invention, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various, non-limiting embodiments of the present invention. In the drawings, common reference numbers indicate identical or functionally similar elements.

DETAILED DESCRIPTION

Figure 1:
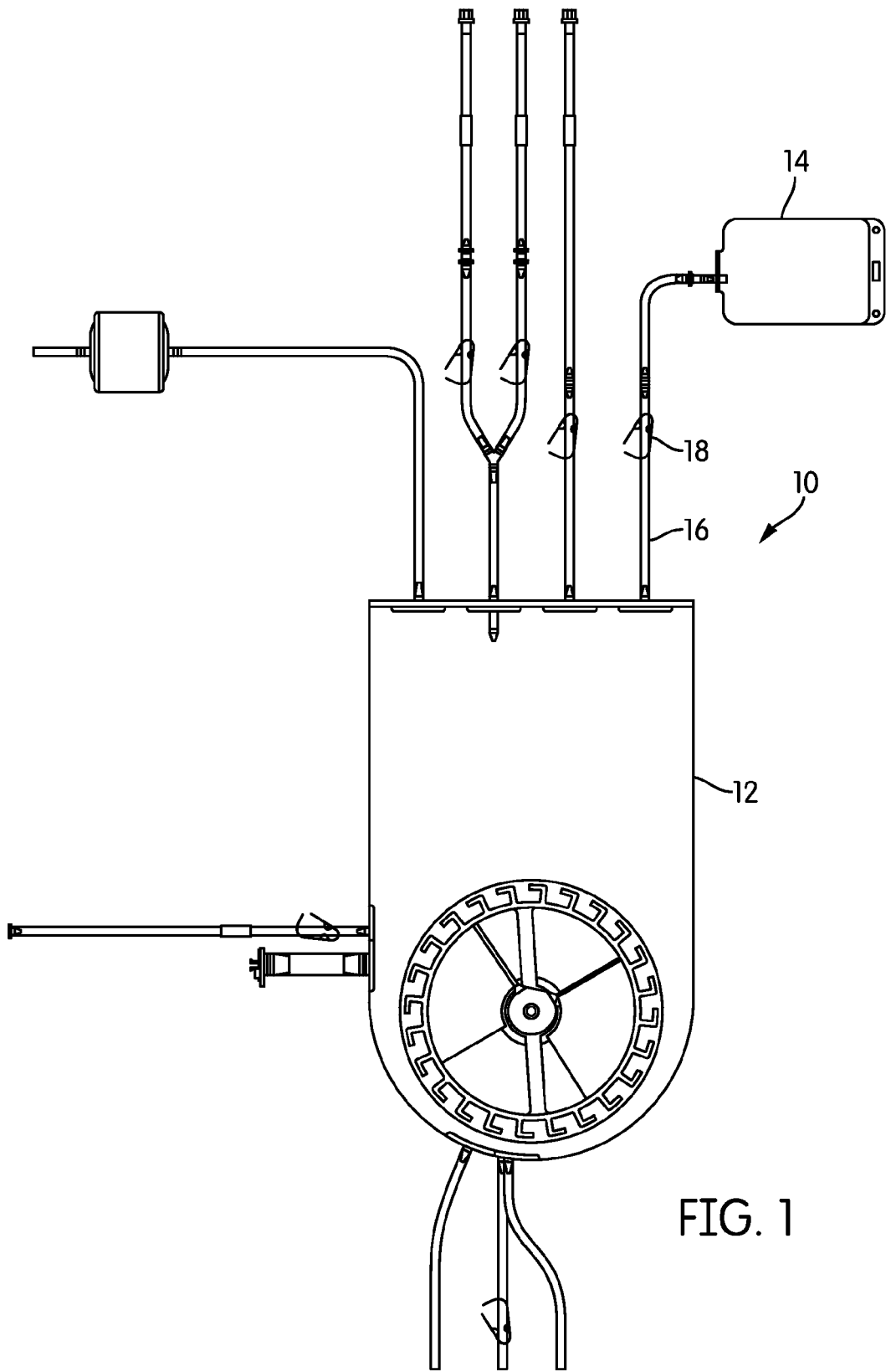
FIG. 1 is a schematic representation of an embodiment of a bioreactor system embodying aspects of the present invention.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the invention and are not intended to be limiting.

Suitable, exemplary, but non-limiting, bioreactor systems, including disposable bioreactor systems, in which concepts embodying aspects of the present invention may be implemented are described in U.S. Pat. No. 7,628,528; International Patent Publication No. WO 2008/133845, U.S. Patent Application Publication No. 2008-0261299; U.S. Pat. No. 7,713,730; International Patent Publication No. WO 2009/132192; U.S. Patent Application Publication No. 2009-0269849; U.S. Pat. No. 7,819,576; U.S. Pat. No. 8,281,672; and U.S. Patent Application Publication No. 2011-0003366, the respective disclosures of which are hereby incorporated by reference.

As noted above, micro-carriers that can withstand gamma radiation at sterilization dosage may be pre-loaded inside a disposable bioreactor vessel assembly by the manufacturer for sterilization by gamma radiation prior to shipping. During shipping and pre-use handling, it is desirable to prevent the dry, powder-like micro-carriers from getting dispersed inside the vessel chamber and sticking to the walls of the chamber, which can lead to a reduction in the amount of micro-carriers that anchorage-dependent cells may utilize for attachment and growth. Therefore, compartmentalizing the micro-carriers within the bioreactor assembly by segregating them from the disposable vessel chamber is a critical part of bioreactor vessel assembly set-up. In addition, adding precise amounts of micro-carriers into the vessel chamber is important to ensure consistent and sufficient amount of surface area is available for cells to grow on.

Accounting for the relative size and consistency of micro-carrier beads, various configurations of micro-carrier compartmentalization may be achieved in disposable bioreactor assemblies, such as described in the following, non-limiting examples.

As shown in FIG. 1, micro-carriers may be stored in a pouch 14 that terminates an addition line 16, e.g., a conduit, to the vessel 12 of a disposable bioreactor assembly 10. The addition line 16 may be clamped or otherwise reversibly blocked by any suitable means, such as a clamp 18, to temporarily prevent micro-carriers from passing through the addition line 16 from the pouch 14 to the vessel 12. Assembly 10 may further include additional lines (e.g., fluid conduits) and associated clamps—not numbered in FIG. 1—for delivering fluids, e.g., water, cell culture medium, nutrients, gas, such as oxygen, carbon dioxide, etc., to or from the vessel 12.

In the context of the present description, a "vessel" is any suitable structure forming an enclosed or enclosable chamber or container to contain a liquid. Exemplary vessels include rigid or semi-rigid tanks or flexible or partially flexible bags made from suitable materials, such as medical grade plastics. The term "pouch" means a discrete enclosed or enclosable container for holding a volume of micro-carriers within a region that is separate from, but connected or connectable to the vessel, e.g., by one or more channels, conduits, etc. and one or more associated ports, connectors, etc. The pouch may be a flexible, collapsible structure, or it may be a rigid or semi-rigid structure. While, in some embodiments and applications, the pouch may have a smaller volumetric capacity than the vessel, in other embodiments, the pouch may have the same or more volumetric capacity than the vessel. Also, in the present description, unless specifically stated or the context dictates otherwise, the terms "liquid" and "fluid" (and "liquid medium" and "fluid medium") are used interchangeably to include pure liquid, a solution, a fluid having a fixed volume, a mixture, including gas entrained in a liquid, a slurry, an emulsion, or any combination(s) thereof.

The embodiment of FIG. 1 simply allows the dry micro-carriers to be dropped into the bioreactor vessel chamber 12 at any point during the cell culture run—prior to or after initial liquid addition to the vessel 12. In some embodiments, addition line 16 may be dedicated to delivering micro-carriers from the pouch 14 to the vessel 12, meaning that no materials other than micro-carriers are delivered to the vessel 12 by the addition line 16. In some embodiments, gravity alone may be sufficient to move the micro-carriers—which may have the consistency of powdered sugar—into the vessel chamber.

Figure 2:
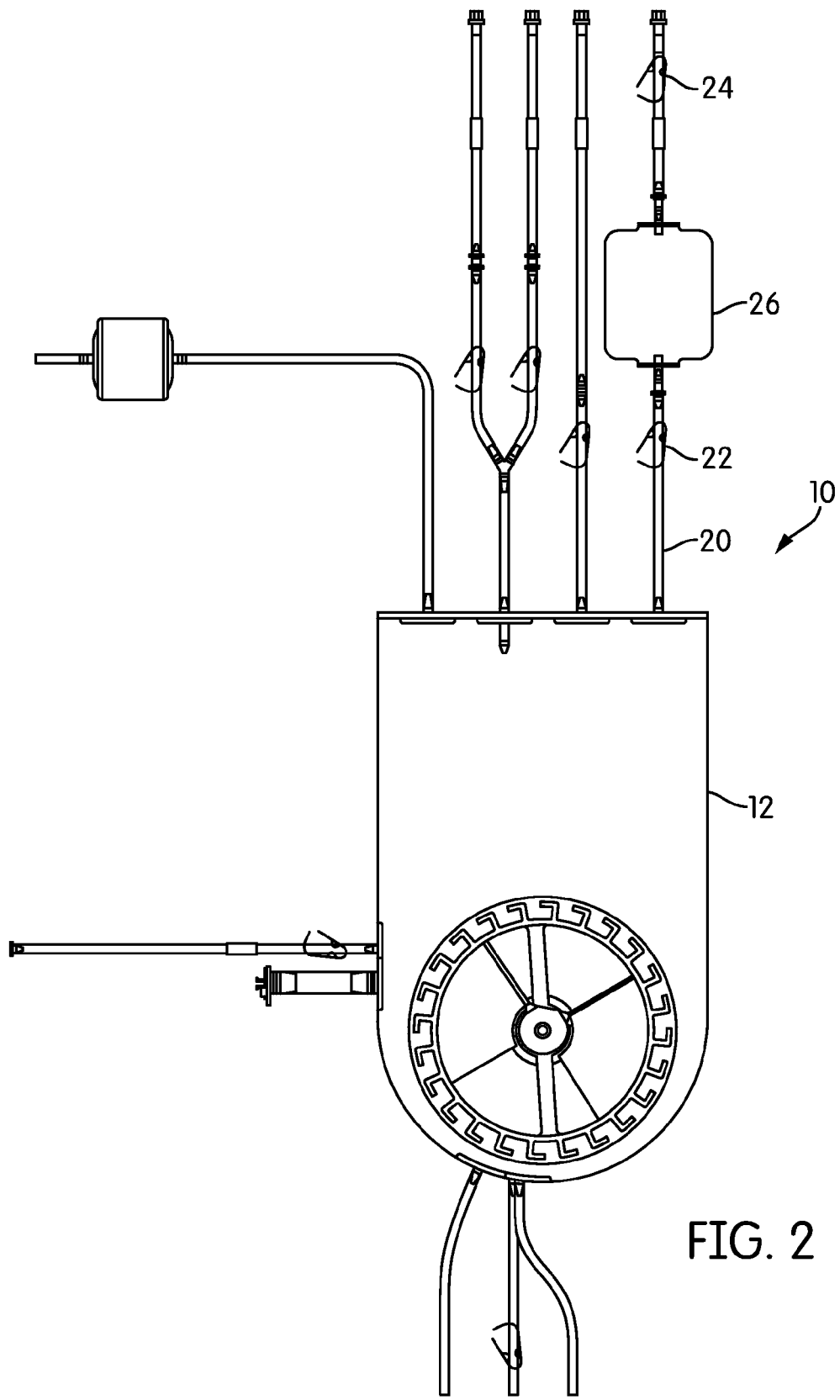
FIG. 2 is a schematic representation of an alternate embodiment of a bioreactor system embodying aspects of the present invention.

As shown in FIG. 2, micro-carriers may be stored in a pouch 26 in-line with an addition line 20 to the vessel 12 of the disposable bioreactor assembly 10. The addition line 20 may be clamped or otherwise reversibly blocked by any suitable means, such as a clamp(s) 22, 24 above and/or below the pouch 26, to temporarily prevent micro-carriers from passing through the addition line 20 from the pouch 26 to the vessel 12. Assembly 10 of FIG. 2 may also include additional lines (e.g., fluid conduits) and associated clamps—not numbered in FIG. 2—for delivering fluids, e.g., water, cell culture medium, nutrients, gas, such as oxygen, carbon dioxide, etc., to or from the vessel 12.

The embodiment of FIG. 2 allows the dry micro-carriers to be dropped into the bioreactor vessel 12, e.g., by gravity, as in the embodiment of FIG. 1, or allows the micro-carriers to be pushed or carried into the bioreactor vessel 12 by means of liquid being pumped into the pouch 26 to flush as much of the micro-carriers from the pouch 26 into the vessel 12 as possible. In this regard clamp 24 above the pouch 26 controls the flow of a flushing liquid into the pouch 26, and clamp 22 located below the pouch 26 (i.e., between the pouch 26 and the vessel 12) controls the flow of micro-carriers and/or fluid flow from the pouch 26 to the vessel 12 whether propelled by gravity or entrained in a flushing liquid. Upper clamp 24 may be opened for a period of time before lower clamp 22 is opened, to thereby allow the flushing liquid to flow into the pouch 26 and be retained within pouch 26 for a period of time to allow the micro-carriers to become adequately dispersed within the flushing liquid before opening the clamp 22 and delivering the mixture of flushing liquid and micro-carriers to the vessel 12.

Typically, the liquid used to push or carry the micro-carriers from the pouch 26 to the vessel 12 would be cell culture medium, but the liquid may also be nutrient solutions, phosphate buffered saline, or even water. The configuration, direction, shape, and number of lines shown in the figures is not intended to be limiting.

Figure 3:
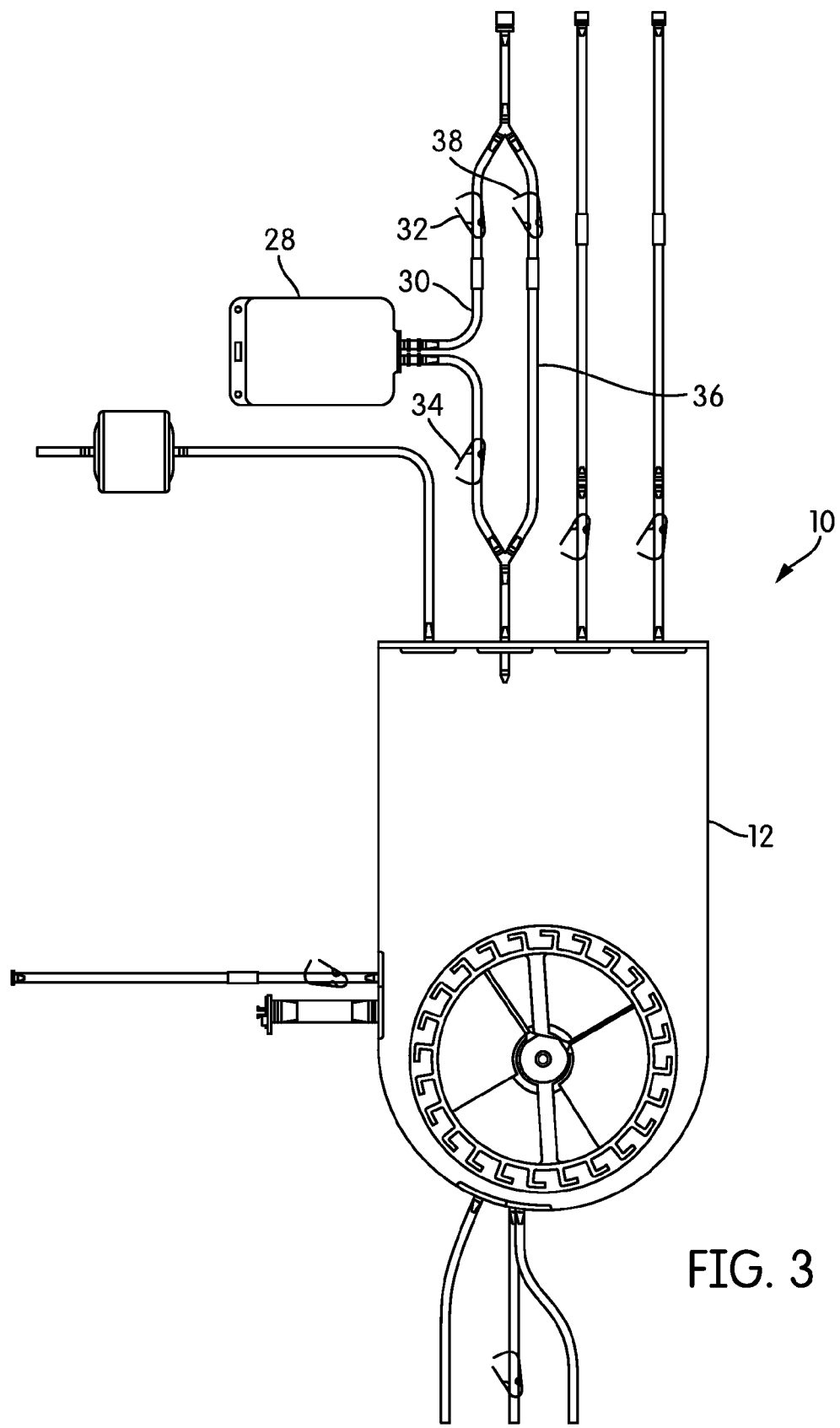
FIG. 3 is a schematic representation of another alternate embodiment of a bioreactor system embodying aspects of the present invention.

As shown in FIG. 3, the micro-carriers may be placed in a pouch 28 on a branched addition line 30 to the vessel 12 of the disposable bioreactor assembly 10. Assembly 10 of FIG. 3 may also include additional lines (e.g., fluid conduits) and associated clamps—not numbered in FIG. 3—for delivering fluids, e.g., water, cell culture medium, nutrients, gas, such as oxygen, carbon dioxide, etc., to or from the vessel 12.

The branched addition line 30 may be clamped or otherwise reversibly blocked by any suitable means, such as a clamp(s) 32, 34 above and below the pouch 28. In this regard, clamp 32 controls the flow of liquid into the pouch 28 and clamp 34 controls the flow of micro-carriers and/or fluid flow from the pouch 28 to the vessel 12 whether propelled by gravity or entrained in a flushing liquid. This embodiment allows most of the liquid to be added to the bioreactor vessel 12, e.g., through a primary addition line 36, prior to adding the last portion of the liquid through the branched line 30 containing the micro-carrier pouch 28, to flush in as much of the micro-carriers into from the pouch 28 into the bioreactor vessel 12 as possible. This embodiment also allows the micro-carriers to be added to a bioreactor vessel 12 already containing liquid, so that the liquid may be mixed as the micro-carriers are introduced into the vessel 12 to prevent the micro-carriers from clumping upon addition.

Thus, in one exemplary implementation of the embodiment of FIG. 3, a clamp 38, or other reversible blocking element in line 36, can be opened, to permit liquid flow through primary addition line 36 into the vessel 12, while clamps 32 and 34 are closed to prevent liquid from flowing through the branched addition line 30 into the pouch 28 and to prevent micro-carriers from flowing from the pouch 28 into the vessel 12. At a desired instance during the cell-culture process, clamp 32 may be opened to allow all or a portion of the liquid (i.e., depending on whether clamp 38 is closed or left fully or partially open while clamp 32 is opened) to flow through branched addition line 30 and into the pouch 28. Clamp 34 is opened to permit a mixture of micro-carriers and flushing liquid to flow from the pouch 28 and into the vessel 12. Upper clamp 32 may be opened for a period of time before lower clamp 34 is opened, to thereby allow the flushing liquid to flow into the pouch 28 and be retained within pouch 28 for a period of time to allow the micro-carriers to become adequately dispersed within the flushing liquid before opening the clamp 34 and delivering the mixture of flushing liquid and micro-carriers to the vessel 12.

Any of the embodiments described above may also be configured without a pouch, if only a small amount of micro-carriers is required. In such a configuration, micro-carriers would be stored in a micro-carrier containment portion of the tubing of the addition line, which is segregatable from the rest of the addition line, and the addition line would be clamped down or otherwise reversibly blocked to prevent the micro-carriers from moving during shipment and handling. The micro-carrier containment portion may be segregated from the rest of the addition line by, for example, one or more clamps or other reversible blocking elements located prior to the micro-carrier containment portion and one or more clamps or other reversible blocking elements located between the micro-carrier containment portion and the vessel.

Any of the embodiments described above may also be configured with an aseptic connection device (e.g. Pall Kleenpak connector, GE ReadyMate connector) on the addition line to allow the pouch or tubing containing micro-carriers to be connected to the vessel of the disposable bioreactor assembly. Thus, the pouch or tubing containing the micro-carriers could be sterilized, stored, transported, etc. separately and independently from the bioreactor assembly and then aseptically connected to the bioreactor vessel prior to use.

Any of the embodiments described above may also be configured in any combination on any number of addition lines on a disposable bioreactor vessel.

Figure 4:
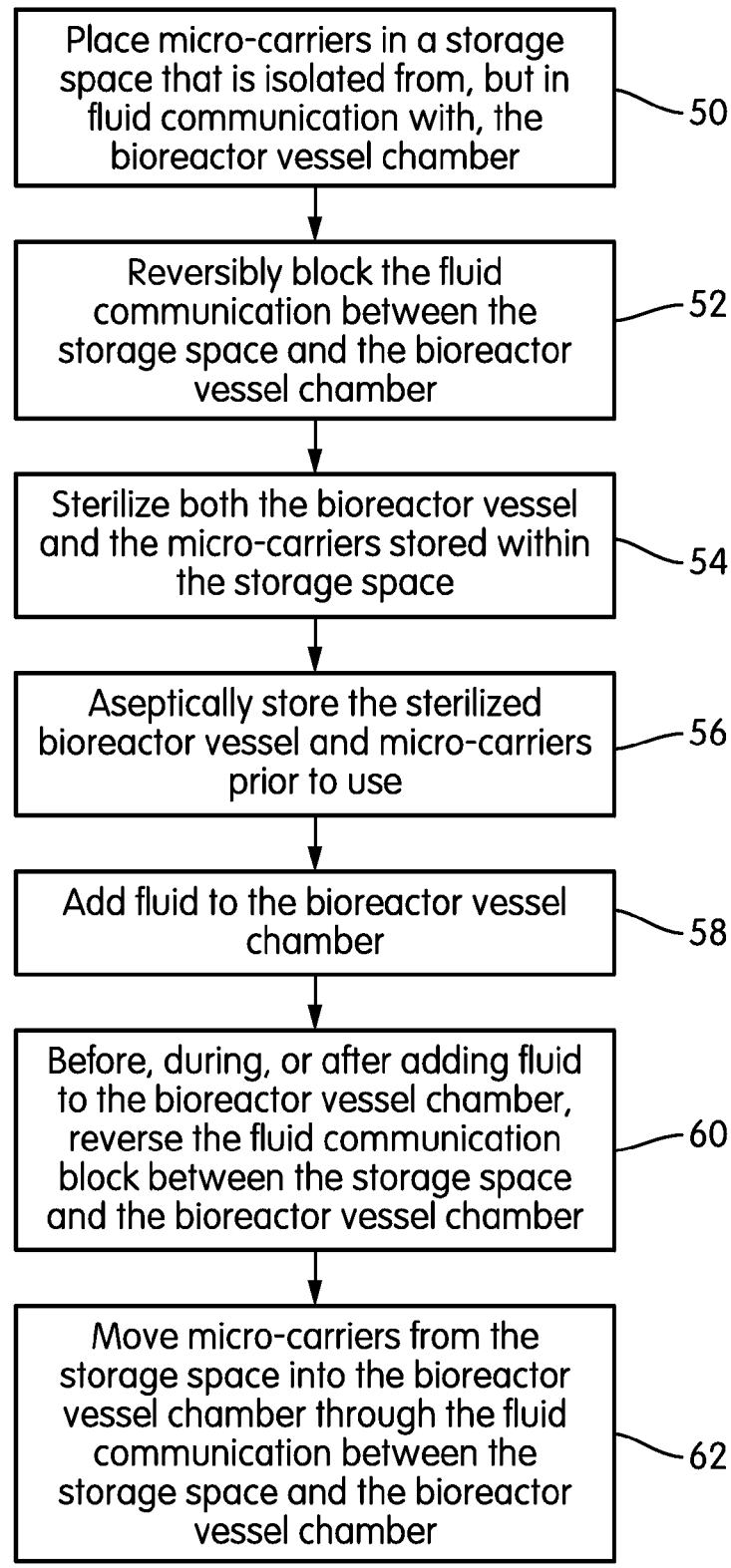
FIG. 4 is a flow chart of a process for providing sterilized micro-carriers to a sterilized vessel chamber of a bioreactor system.

A flow chart illustrating the steps of a process for employing micro-carriers into a bioreactor assembly is shown in FIG. 4. At step 50, micro-carriers are placed in a storage space that is isolated from, but in fluid communication with, the bioreactor vessel chamber. In the context of the present description, a first and a second location are in "fluid communication" if there is a structure between the two locations defining, e.g., a conduit, channel, passage, opening, etc., that facilitates fluid flow from the first location to the second location. For example, as explained above, the micro-carriers may be placed in a pouch that is connected to the bioreactor vessel chamber by an addition line, or the micro-carriers may be placed within the addition line itself.

At step 52, the fluid communication between the storage space and the bioreactor vessel chamber is reversibly blocked, such as by one or more clamps as described above, to retain the micro-carriers within the storage space and prevent the micro-carriers from entering the bioreactor vessel chamber.

At step 54, both the bioreactor vessel and the micro-carriers stored within the storage space are sterilized, for example, by exposing the vessel and micro-carriers to sterilizing gamma radiation of a prescribed strength and for a prescribed period of time, typically between 25-40 kiloGray of dosage used for medical device sterilization. After sterilization, at step 56, the vessel and micro-carriers are aseptically stored prior to use.

At step 58, when the bioreactor is ready for use, fluid medium is added to the bioreactor vessel chamber. The fluid medium may include cell culture medium or nutrient solutions, or a combination of the two, as well as possibly other fluids, for example, as noted above.

At step 60, the fluid communication block between the storage space and the bioreactor vessel chamber is removed, such as by removing one or more clamps, to thereby open the fluid communication between the storage space and the bioreactor vessel chamber and thereby permit the micro-carriers to flow into the bioreactor vessel chamber. Step 60 may be performed before, during, or after step 58—adding fluid to the bioreactor vessel chamber.

At step 62, with the fluid communication between the storage space and the bioreactor vessel chamber established, the micro-carriers are moved from the storage space to the bioreactor vessel chamber. Step 62 may be performed by gravity or by a flushing liquid—e.g., cell culture medium and/or nutrient solution—through the storage space to entrain the micro-carriers and carry the micro-carriers into the bioreactor vessel chamber. That is, step 62 can be performed using any of the embodiments and associated procedures described above in connection with FIG. 1, 2, or 3.

After cells have grown to a sufficient density on micro-carriers within a bioreactor vessel, it may be desirable to remove the spent cell culture medium from the bioreactor for a variety of reasons, including harvesting the drug substance (secreted protein of interest) at the end of the run, as well as performing an exchange of spent medium with fresh medium. In such cases, it is desirable to remove only the spent medium from the bioreactor vessel while retaining the micro-carriers with attached cells within the bioreactor vessel chamber.

In traditional bioreactors, no simple solution exists for removing spent medium without also removing micro-carriers from the bioreactor chamber. Filters, such as depth filters and membrane filters, may be provided at fluid outlets to capture micro-carriers while allowing the spent medium to pass thorough the outlet, but micro-carriers would inevitably accumulate on the pores of the filters thereby clogging the filter. Other, means for separating the micro-carriers from the spent media involve the use of perfusion devices whereby the fluid media/micro-carrier mixture is caused to flow, outside the bioreactor chamber, into a perfusion device in which a pressure differential is created to cause the spent media to flow through a porous membrane that traps the micro-carriers. The separated micro-carriers then need to be recirculated in the bioreactor chamber. The use of perfusion devises adds an undesirable level of complexity to the bioreactor.

In the bioreactor systems described in the documents incorporated by reference above, a pneumatically driven mixing wheel rotates about a horizontal axis within a vessel having a curved bottom and generates a significant tangential fluid flow along the outer periphery of the rotating wheel. This tangential liquid flow serves to create a cross-flow relative to the curved bottom surface of the vessel that sweeps micro-carriers away from the pores of a filter element as the spent medium is being removed from the chamber, thereby preventing the micro-carriers from clogging the filter pores.

Figure 5:
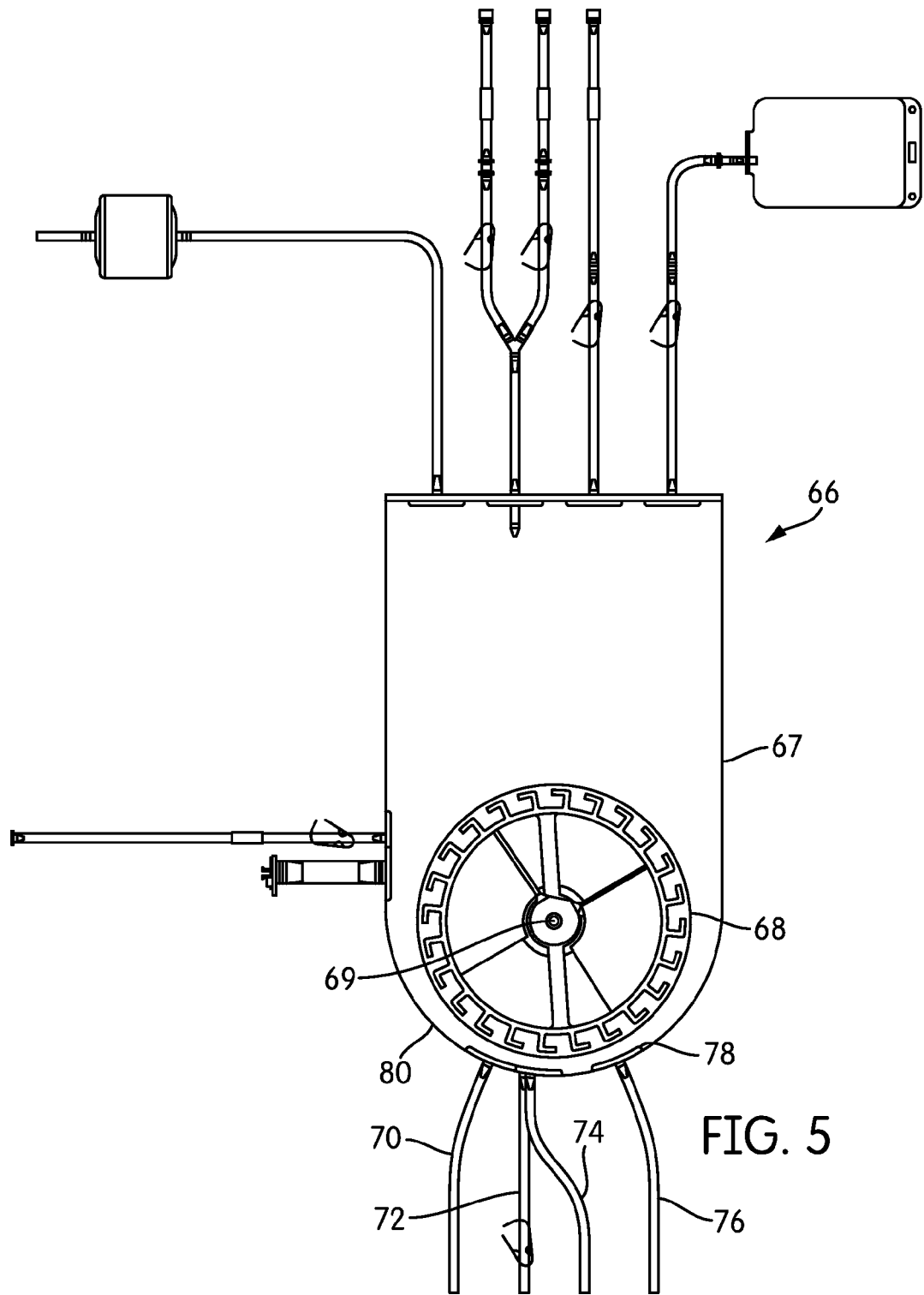
FIG. 5 is a schematic representation of another alternate embodiment of a bioreactor system embodying aspects of the present invention showing features for retaining micro-carriers within a vessel chamber as fluids are removed from the chamber.
Figure 6:
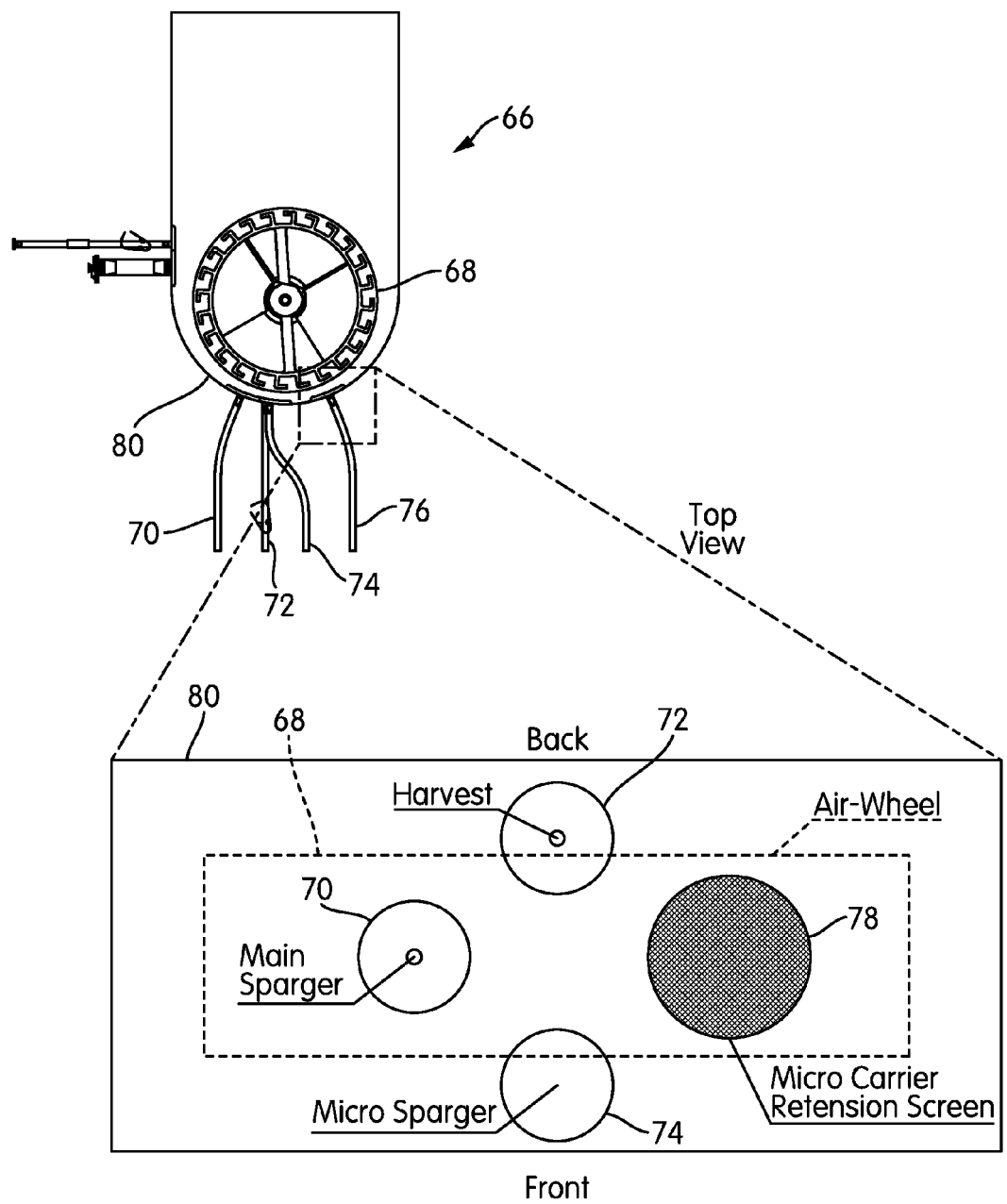
FIG. 6 is a schematic representation of a bioreactor chamber with an exploded, enlarged view of the bottom of the chamber, showing features for retaining micro-carriers within a vessel chamber as fluids are removed from the chamber.

As shown in FIGS. 5 and 6, a bioreactor system 66 may include a vessel 67 with a curved bottom 80 and a mixing wheel 68 that is rotatable about axis 69 disposed therein. Air, or other gas, is injected into the vessel to pneumatically drive the wheel 68 via a main sparger 70 that terminates at the curved bottom 80 below the wheel 68. Additional gas may be injected into the vessel 67 through a micro-sparger 74. A harvest port 72 allows for the final removal of the micro-carriers—and cells carried thereon—from the vessel 67.

To remove fluid medium from the vessel 67 without also removing the micro-carriers, a media removal port 76 on the bioreactor vessel 67 may be configured with a retention screen 78 having a pre-determined and controlled pore size to effectively retain the micro-carriers in the culture while removing spent medium. Due to the relatively large size of the micro-carriers, the retention screen 78 may be relatively coarse thereby facilitating the efficient removal of the fluid medium from the vessel 67. The pore sizes of the micro-carrier retention screen 78 are slightly smaller than the diameter of the micro-carriers to ensure maximum rate of liquid removal and maximum percentage of micro-carrier retention. The exact pore size would depend not only on the mean diameter of the particular micro-carriers but also the typical size distribution of the micro-carrier beads. The configuration, direction, shape, and number of lines shown in the figures is not intended to be limiting.

The media removal port 76 and retention screen 78 are disposed below the mixing wheel 68 on the curved surface 80. This defines a relatively small width between the outer periphery of the mixing wheel 68 and the retention screen 78, which is a region of high tangential fluid flow. This tangential flow creates a sweeping action that prevents the micro-carriers from settling on the retention screen 78 and clogging the pores of the retention screen 78 while allowing media fluid to pass through the retention screen 78 and out the media removal port 76. While fluid is being removed through the media removal port 76, fresh media may be added to the vessel 67 through one or more addition ports to create a steady-state equilibrium of fluid volume within the vessel 67.

The tangential speed of the fluid flow over the retention screen 78 on the curved surface 80 will depend, in some respects, on the size of the gap between the perimeter of the mixing wheel 68 curved surface 80. In general, the smaller the gap, the higher the speed of tangential flow within the gap. Also, in general, the greater the tangential flow speed, the greater the sweeping action preventing the micro-carriers from settling on the retention screen 78 and clogging the pores of the retention screen 78. On the other hand, tangential flow creates a shear force tending to separate cells from the micro-carrier, and thus, it may not be desirable to generate excessive tangential flow speed. In addition, lowering the mixing wheel 68 within the vessel to bring the perimeter of the mixing wheel 68 into closer proximity to the curved surface 80 and thus reduce the size of the gap can result in the mixing wheel 68 having less mixing effect on the fluid in the upper portion of the vessel. Thus, the additional tangential speed that can be achieved by lowering the mixing wheel 68 and reducing the gap between the mixing wheel 68 and the curved surface 80 should be balanced against the need to achieve effective mixing throughout the vessel.

The tangential speed will also depending on the size of the mixing wheel 68—for two wheels rotating at the same rate, the wheel with the larger diameter will have the greater perimeter speed.

By way of non-limiting examples, the gaps, in centimeters, between the mixing wheel and the curved bottom surface for vessels of different sizes, in liters, may be as follows:

3 L: 1 cm
15 L: 1.5 cm
80 L: 3 cm
500 L: 9 cm.

The retention screen 78, with controlled pore size, may be manufactured, for example, simply by puncturing plastic film of choice with a fine needle. This element would then be attached to a media removal port 76 on the bottom 80 of the bioreactor vessel 67 using adhesive or a heat-welding process.

Figure 7:
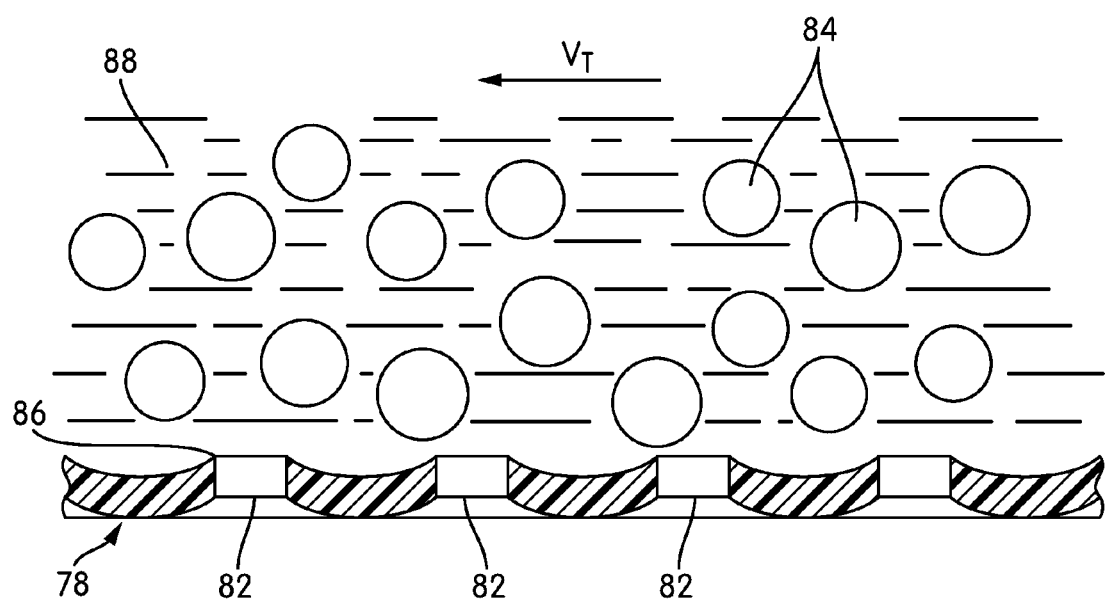
FIG. 7 is an enlarged, cross-section of a portion of a micro-carrier retention screen having a plurality of pores and a fluid with a plurality of micro-carriers entrained therein flow past the screen.

FIG. 7 is an enlarged cross-section of a portion of the retention screen 78 having a plurality of pores 82. Micro-carriers 84 of varying sizes flow within fluid media 88 with a tangential velocity of VT. The tangential flow prevents the micro-carriers 84 from settling on and clogging the pores 82, while allowing fluid 88 to pass through the pores 82. In one embodiment, as shown in FIG. 7, the pores 82 are formed in a convex manner with respect to the fluid media side of the retention screen 78 and have a perimeter 86 that is raised into the media 88 (i.e., into the chamber of the vessel 67). Such a pore configuration can be created, for example, by puncturing a plastic sheet toward the fluid media side or by injection molding a retention screen having pores 82 with a raised perimeter 86 surrounding each pore. This convex pore configuration further prevents the micro-carriers 84 from settling in and clogging the pores 82.

In another embodiment, the retention screen would be larger in size or in different shape than the flange of the media removal port, preventing the screen from being heat-welded or glued directly onto the media removal port. In this design, the retention screen of interest would simply be attached directly to the curved bottom wall 80 of the bioreactor vessel 67 using adhesive or heat-weld in a way that would cover the media removal port on the vessel.

At harvest, cells are typically detached from micro-carriers by chemical means, e.g., by exposing the micro-carriers and attached cells to an enzyme, such as trypsin, which cleaves the bond between the cell surface and micro-carrier surface through hydrolysis and frees up the cells to be harvested. To facilitate this detachment process while preserving the integrity of the cell membrane, a controlled amount of shear force may be applied to the culture. Typically, the shear force would be applied to the micro-carriers outside the cell culture vessel.

In accordance with aspects of this invention, the process of separating the cultured cells from the micro-carriers and harvesting the separated cells can be performed in the bioreactor. The culture would be concentrated first by removing excess spent medium from the media removal port. Trypsin, or another suitable cleaving enzyme, is then added while the vessel is agitated, e.g., by a mixing wheel, such as mixing wheel 68, at a controlled speed to provide both chemical and mechanical means for cell detachment.

This step is similar to a medium exchanged whereby spent medium is removed and replaced by un-spent medium—as described above—except, in this step of the process, the spent medium is removed and is replaced by a volume of enzyme solution. The amount of spent medium that is removed from the vessel prior to adding the enzyme solution may depend on a number of factors, such as the concentration of the enzyme—and therefore the amount of enzyme solution that must be added. In a non-limiting embodiment, most of the spent medium, e.g., 80-90%, may be removed from the vessel prior to adding an amount of enzyme solution to the vessel.

The speed at which the mixing wheel 68 is rotated may be substantially the same speed it is rotated during the cell culture process. In other implementations, the speed may be greater than the speed used during the cell culture process to increase the shear forces.

The retention screen 78, which may have a pre-determined pore size smaller than the size of the micro-carriers (e.g., on the order of 100 micron in diameter) but larger than the size of the cells (e.g., on the order of 10 micron in diameter) would allow cells to be collected from the media harvest port, while retaining the micro-carriers in the vessel.

Thus, the presence of the retention screen 78 in the bioreactor allows a one-step process which can: 1) enhance the growth of anchorage-dependent cells on micro-carriers using medium exchange or perfusion during the cell cultivation phase; 2) allow enzymatic treatment for cell detachment in the same vessel by removing the culture medium while retaining micro-carriers and attached cells and replacing the cell culture media with enzyme solution (e.g., trypsin); and 3) after separation of the cultured cells from the micro-carriers, harvest the cell-containing solution through the retention screen while retaining the separated micro-carriers inside the bioreactor vessel. Currently, this cell recovery process is performed in separate steps in various containers: culture cells in the cell culture vessel, separate cells from micro-carriers in an enzyme treatment vessel, and separate empty micro-carries from cells by centrifugation, etc. Aspects of the invention can simplify the entire process from cell cultivation, enzyme treatment with physical shear force, and cell recovery from the micro-carrier beads in an one-step process.

While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the present invention is deemed to include all modifications and variations encompassed within the spirit and scope of the following appended claims.

The invention claimed is:

1. A bioreactor system for a cell culture procedure, comprising:
   a bioreactor vessel configured to contain a fluid cell culture media, cultured cell material and micro-carriers of a predetermined diameter, the vessel being formed of a medical grade plastic having a plurality of outer walls;
   a fluid agitator configured to move within the vessel rotatable about a horizontal axis so as to create a fluid flow of the cell culture media and micro-carriers within the vessel, including an area of fluid flow tangent to a first one of the outer walls located below the fluid agitator; and
   a port open to the first outer wall configured for removing fluid cell culture media from the vessel and comprising a retention screen formed by pores in and opening through the first outer wall, wherein the retention screen is oriented parallel to the tangent flow and includes pores sized to retain the micro-carriers in the vessel while fluid cell culture media is removed from the vessel via the media removal port, wherein the tangent flow prevents the micro-carriers from settling on and clogging the pores.

2. The bioreactor system according to claim 1, wherein the retention screen comprises a plurality of pores formed in a convex manner with respect to a fluid media side of the retention screen and having a perimeter that is raised toward an interior of the vessel.

3. The bioreactor system according to claim 2, wherein the retention screen is injection molded such that the pores have a raised perimeter toward the fluid media side of the retention screen.

4. The bioreactor system according to claim 1, wherein the retention screen has pores of at least 10 microns in diameter.

5. The bioreactor system according to claim 4, wherein the retention screen has pores smaller than the predetermined diameter of the micro-carriers.

6. The bioreactor system according to claim 5, wherein the predetermined diameter of the micro-carriers is about 100 micron.

7. The bioreactor system according to claim 1, wherein the first outer wall of the vessel is a curved bottom wall and the fluid agitator comprises a mixing wheel that creates the area of flow tangent to the curved bottom wall.

8. The bioreactor system according to claim 7, wherein the system includes a main sparger that terminates at the curved bottom wall below the mixing wheel and air or other gas is injected into the vessel through the main sparger to pneumatically drive the wheel.

9. The bioreactor system according to claim 1, wherein the vessel is a flexible or partially flexible disposable bag.

10. The bioreactor system according to claim 1, further including:
    a micro-carrier container configured to store micro-carriers;
    one or more fluid conduit lines connecting the micro-carrier container and the vessel such that the micro-carrier container is in fluid communication with the vessel,
    wherein the one or more fluid conduit lines is reversibly blocked to block fluid flow in the one or more lines, and
    wherein the micro-carrier container and the vessel are configured to allow the micro-carriers to be dropped into the vessel at any point during a cell culture procedure when the one or more fluid conduit lines are unblocked.

11. The bioreactor system according to claim 10, wherein the micro-carrier container comprises a pouch connected to the one or more fluid conduit lines.

12. The bioreactor system according to claim 10, wherein the micro-carrier container comprises a segregatable portion of the one or more fluid conduit lines.

13. The bioreactor system according to claim 10, wherein the one or more fluid conduit lines comprises a main addition line and the micro-carrier container terminates the main addition line, and wherein the system further comprises:
    a reversible clamp disposed on the main addition line between the micro-carrier container and the vessel and configured to temporarily prevent micro-carriers from passing through the main addition line from the micro-carrier container to the vessel, and
    wherein the micro-carrier container, the vessel, the main addition line, and the blocking element are configured such that gravitational force is sufficient to cause micro-carriers to pass from the micro-carrier container to the vessel via the main addition line.

14. A bioreactor system for a cell culture procedure, comprising:
    a bioreactor vessel configured to contain a fluid cell culture media, cultured cell material and micro-carriers of a predetermined diameter, the vessel is a flexible or partially flexible disposable bag having a curved bottom wall;

a mixing wheel within the vessel rotatable about a horizontal axis such that an outer extent of the mixing wheel creates a fluid flow of the cell culture media and micro-carriers within the vessel, including an area of flow tangent to the curved bottom wall; and a port open to the curved bottom wall configured for removing fluid cell culture media from the vessel and comprising a retention screen, wherein the retention screen includes pores in and opening through the curved bottom wall sized to retain the micro-carriers in the vessel while fluid cell culture media is removed from the vessel via the media removal port.

15. The bioreactor system according to claim 14, wherein the retention screen comprises a plurality of pores formed in a convex manner with respect to a fluid media side of the retention screen and having a perimeter that is raised toward an interior of the vessel.

16. The bioreactor system according to claim 15, wherein the retention screen is injection molded such that the pores have a raised perimeter toward the fluid media side of the retention screen.

17. The bioreactor system according to claim 14, wherein the retention screen has pores of at least 10 microns in diameter.

18. The bioreactor system according to claim 17, wherein the retention screen has pores smaller than the predetermined diameter of the micro-carriers.

19. The bioreactor system according to claim 18, wherein the predetermined diameter of the micro-carriers is about 100 micron.

20. The bioreactor system according to claim 14, wherein the system includes a main sparger that terminates at the curved bottom wall below the mixing wheel and air or other gas is injected into the vessel through the main sparger to pneumatically drive the wheel.

21. The bioreactor system according to claim 14, wherein the retention screen is oriented parallel to the tangent flow.

22. The bioreactor system according to claim 14, wherein the vessel is formed of a medical grade plastic.

23. The bioreactor system according to claim 14, further including:

a micro-carrier container configured to store micro-carriers;

one or more fluid conduit lines connecting the micro-carrier container and the vessel such that the micro-carrier container is in fluid communication with the vessel, wherein the one or more fluid conduit lines is reversibly blocked to block fluid flow in the one or more lines, and wherein the micro-carrier container and the vessel are configured to allow the micro-carriers to be dropped into the vessel at any point during a cell culture procedure when the one or more fluid conduit lines are unblocked.

24. The bioreactor system according to claim 23, wherein the micro-carrier container comprises a pouch connected to the one or more fluid conduit lines.

25. The bioreactor system according to claim 23, wherein the micro-carrier container comprises a segregatable portion of the one or more fluid conduit lines.

26. The bioreactor system according to claim 23, wherein the one or more fluid conduit lines comprises a main addition line and the micro-carrier container terminates the main addition line, and wherein the system further comprises:

a reversible clamp disposed on the main addition line between the micro-carrier container and the vessel and configured to temporarily prevent micro-carriers from passing through the main addition line from the micro-carrier container to the vessel, and wherein the micro-carrier container, the vessel, the main addition line, and the blocking element are configured such that gravitational force is sufficient to cause micro-carriers to pass from the micro-carrier container to the vessel via the main addition line.

* * * * *